United States Patent [19]

Carter

[11] Patent Number: 4,589,280

[45] Date of Patent: May 20, 1986

[54] FLUID FLOW METER UTILIZING PRESSURE SENSING

[75] Inventor: Garry L. Carter, Racine, Wis.

[73] Assignee: Medical Engineering Corporation, Racine, Wis.

[21] Appl. No.: 666,358

[22] Filed: Oct. 30, 1984

Related U.S. Application Data

[63] Continuation-in-part of Ser. No. 447,759, Dec. 8, 1982, abandoned.

[51] Int. Cl.$^4$ .............................................. G01F 3/38
[52] U.S. Cl. ..................................... 73/226; 128/760; 604/67; 604/248
[58] Field of Search ................. 73/861, 222, 226, 299, 73/290 B; 128/760, 761, DIG. 12; 604/65, 67, 246, 247, 248; 137/134, 141, 142

[56] References Cited

U.S. PATENT DOCUMENTS

| Re. 30,607 | 5/1981 | Manschot et al. ................ | 128/762 |
|---|---|---|---|
| 2,814,950 | 12/1957 | Lawlor ................ | 73/216 |
| 3,726,140 | 4/1973 | Barbee ................ | 73/299 |
| 3,919,455 | 11/1975 | Sigdell et al. ................ | 73/226 |
| 3,949,745 | 4/1976 | Howell ................ | 137/135 X |
| 3,986,398 | 10/1976 | Laymance ................ | 73/299 |
| 4,000,649 | 1/1977 | Hanifl ................ | 73/219 |
| 4,020,690 | 5/1977 | Samuels et al. ................ | 73/299 |
| 4,051,431 | 9/1977 | Wurster ................ | 324/61 R |
| 4,084,435 | 4/1978 | Weik et al. ................ | 73/299 |
| 4,085,616 | 4/1978 | Patel et al. ................ | 73/215 |
| 4,099,412 | 7/1978 | Nehrbass ................ | 73/209 |
| 4,187,722 | 2/1980 | Layton ................ | 73/229 |
| 4,200,112 | 4/1980 | McWhorter ................ | 128/761 |
| 4,241,017 | 12/1980 | Balistreri et al. ................ | 422/58 |
| 4,301,813 | 11/1981 | Merry et al. ................ | 128/762 |
| 4,343,316 | 8/1982 | Jesperson ................ | 128/771 |
| 4,355,638 | 10/1982 | Iwatschenko et al. ..... | 128/DIG. 12 |

FOREIGN PATENT DOCUMENTS 2031158 4/1980 United Kingdom ................. 73/226

OTHER PUBLICATIONS

"Analysis of Micturition, A New Method of Recording the Voiding of the Bladder", *Acta Chirargica Scandinavica*, (1956), Von Garrelts, B., pp. 326-340.

"Uroflometry in Urological Diagnosis", Joseph J. Kaufman, *California Medicine*, vol. 95, Aug. 1961, pp. 100-103.

"A New Uroflowmeter for Routine Clinical Use", *Biomedical Engineering*, vol. 10, No. 1, (Jan. 1975), Randall, pp. 21-24.

Primary Examiner—James L. Rowland
Assistant Examiner—Brian R. Tumm
Attorney, Agent, or Firm—Quarles & Brady

[57] ABSTRACT

An improved fluid flow meter for measuring a liquid flow rate is disclosed. It comprises a container having an interior cavity, an inlet opening, a vent opening, a first passageway and a second passageway. The first passageway has an upper opening which is sealed by a pressure transducer and has a lower opening which opens into the interior cavity below the inlet and vent openings. A pressure signal produced in the first passageway by liquid in the cavity is converted into a flow rate by a processor which is connected to the pressure transducer. The second passageway has a lower opening in communication with the interior cavity above the lower opening of the first passageway and an upper opening below the upper opening of the first passageway which is connected to a downwardly depending drain tube to drain the level of liquid in the cavity down by siphon action. In one embodiment the vent opening and the second passageway are in communication with the upper portion of a second cavity which is provided below the first cavity and has a lower outlet opening.

3 Claims, 5 Drawing Figures

FLUID FLOW METER UTILIZING PRESSURE SENSING

This is a continuation-in-part of application Ser. No. 447,759 filed Dec. 8, 1982, now abandoned.

FIELD OF THE INVENTION

This invention relates to fluid flow meters and more particularly to a fluid flow meter for medical applications.

BACKGROUND OF THE INVENTION

Diagnosis of kidney and urinary tract infections is often facilitated by a knowledge of the patient's urinary flow rate. Urinary flow rate data is particularly important in critical care situations, and in particular when the patient has just undergone surgery since the patient may not be conscious and able to verbalize any symptoms. In critical care situations, urine is usually continuously drained from the body via a Foley type catheter and the urine output is usually determined by visually observing the amount of urine drained from the patient via the catheter into a drainage receptacle.

Examples of prior art drainage receptacles for enabling the quantity of urine drained via a Foley type catheter to be determined are found in U.S. Pat. Nos. 4,301,813, 4,095,589, 4,085,616 and 4,000,649. Each of the prior art drainage receptacles described in the above listed patents includes a transparent urine receiving chamber having a graduated scale thereon for indicating the quantity of urine entering the chamber. The urine flow rate is determined in such devices by observing the quantity of urine entering the chamber of the drainage receptacle over a period of time.

While the prior art devices are satisfactory for this purpose, there are several disadvantages associated with measuring urine in this manner. The most obvious disadvantage is that the urine flow is detected visually. This requires either a nurse, a doctor or a technician to observe the patient for a set period of time. In practice, a nurse generally records the volume of urine at 15 minute intervals. However, inaccuracies may arise due to failure to maintain an exact interval between observations. In addition, an exact measurement may not always be obtained due to the imprecisions in reading the drainage receptacle scale. More importantly, the use of prior art urine flow measuring techniques do not provide an instantaneous measure of excessive urine output unless the nurse, doctor or technician is present to observe the excessive urine output.

BRIEF SUMMARY OF THE INVENTION

Briefly, in accordance with the preferred embodiment of the invention, a fluid flow meter for measuring fluid flow and in particular for measuring urine flow includes a container comprising an interior chamber which defines an interior cavity. The interior chamber has an upper portion with an inlet opening for admitting a liquid, such as urine, into the cavity. The upper portion is also provided with a vent opening for admitting air at atmospheric pressure into the cavity. A first conduit defines a passageway within the container which has a lower opening which opens into the interior cavity below the inlet and vent openings and which has an upper opening which is suitable to mount a pressure transducer to measure the air pressure in the first passageway. The air pressure in the first passageway varies according to the volume of liquid in the interior cavity so that the pressure transducer output signal can be used to determine the flow rate of liquid into the container.

To prevent the container from overflowing, a second passageway can be provided having a lower outlet opening above the lower opening of the first passageway and having an upper outlet opening below the upper opening of the first passageway. The upper outlet opening of the second passageway is suitable to be connected to a urine drainage bag below the container. With this structure, when the level of urine reaches the level of the upper outlet opening of the second passageway, urine will be drained from the interior cavity by siphon action into the urine drainage bag.

A container of the invention thus described can be inexpensively manufactured from polystyrene plastic or the like so as to make it economical to dispose of after use, thereby avoiding the need for cleaning.

The fluid flow meter described above can also be advantageously modified to yield a meter pump apparatus for intravenous fluid which not only measures the rate of intravenous fluid flow but which also precisely delivers the fluid flowing therethrough while assuring total sterility. To obtain such a meter pump apparatus, a second chamber defining a second cavity is added to the fluid flow meter previously described so that the second cavity is located in part below the first cavity. The second cavity has an outlet at its lower end, the outlet being coupled by a feed tube or the like to the patient so that intravenous fluid may be carried from the second cavity into the patient. The upper portion of the second cavity is in communication with the first cavity via two passageways. One of those passageways is an equalizer passageway which is in communication with the vent opening and seals the vent opening from the atmosphere. The other passageway is a siphon passageway which communicates with the upper outlet opening of the second passageway to help provide the siphon action which lowers the level of liquid within the first cavity. When a partial vacuum is developed in the container by priming it and a liquid is introduced into the first cavity through the inlet, the air in the first cavity is forced therefrom into the second cavity via the equalizer passageway to effectively pump the liquid in the second cavity into the patient. The continued introduction of liquid into the first cavity causes the first cavity to fill to the level of the upper outlet opening of the second passageway so that the liquid is transferred from the first cavity to the second cavity by siphon action via the siphon passageway to replenish the volume of liquid in the second cavity. By regulating the flow rate of liquid entering the first cavity through the use of a flow control valve, the volume of fluid entering the patient can be precisely metered. Since the entire system is closed, sterility is assured.

It is an object of the invention to provide a fluid flow meter for measuring a rate of fluid flow;

It is yet another object of the invention to provide a fluid flow meter for measuring a rate of fluid flow electrically;

It is yet another object of the invention to provide a fluid flow meter for electrically measuring a rate of fluid flow which is inexpensive to manufacture so as to make disposal after use economical.

It is yet another object of the present invention to provide an improved meter pump apparatus for not only measuring fluid flow therethrough but for pumping fluid therethrough.

It is yet another object of the present invention to provide a meter pump for not only measuring the rate of fluid flow but for precisely metering fluid flow therethrough;

Other objects and advantages will become apparent from the following detailed description and from the drawings.

DETAILED DESCRIPTION OF THE PREFERRED EMBODIMENTS

Figure 1:
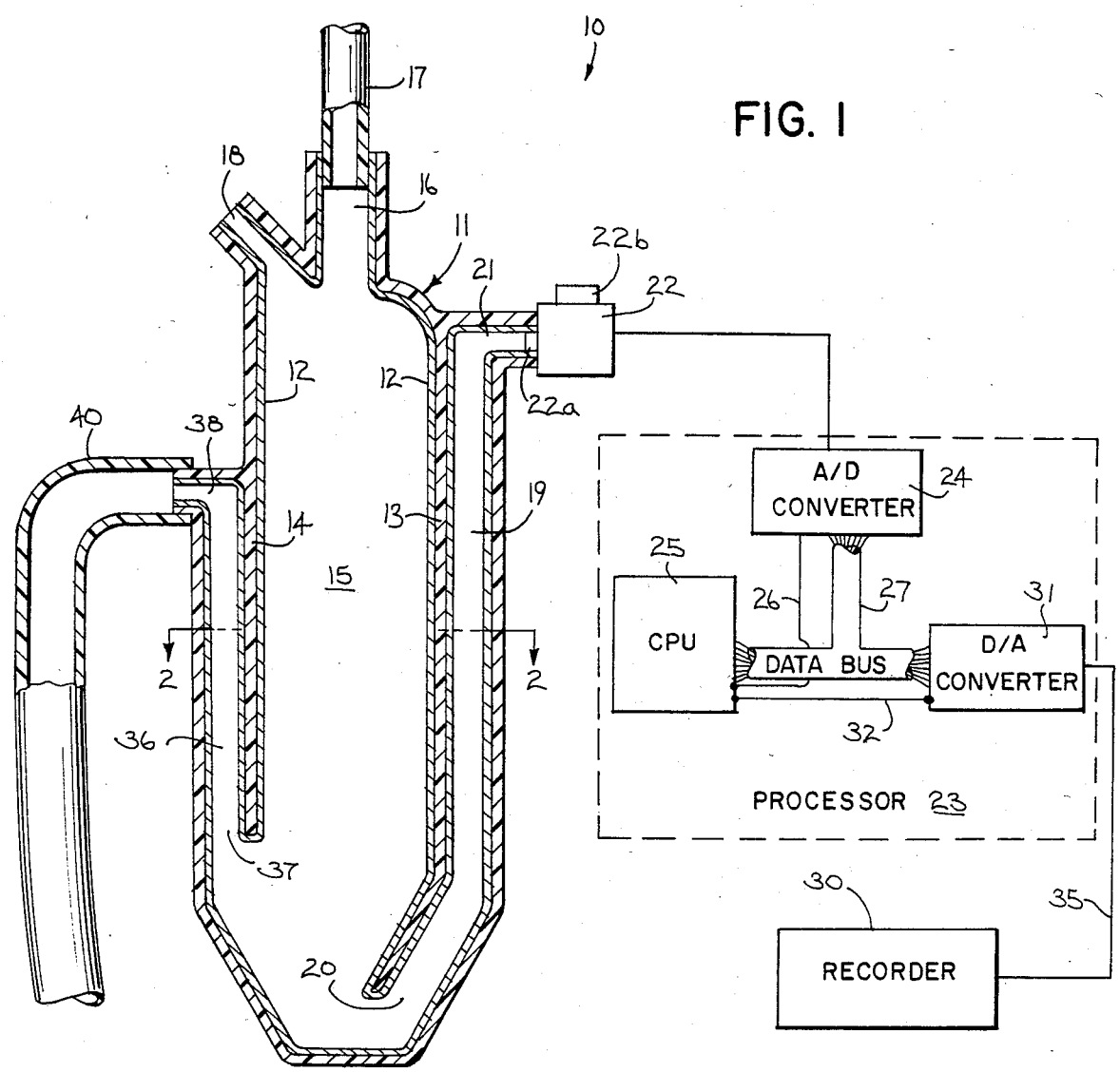
FIG. 1 is a block diagram of a fluid flow meter apparatus of the present invention.
Figure 2:
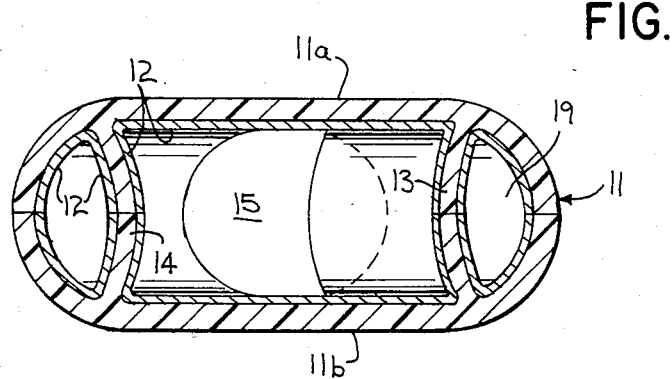
FIG. 2 is a cross-sectional view of the container of the fluid flow meter apparatus of FIG. 1 taken along the plane of the line 2—2 thereof.

FIG. 1 illustrates a fluid flow meter 10 of the present invention which includes a container 11. Referring also to FIG. 2, the container 11 is made up of two rigid wall sections 11a and 11b which are joined at their edges. The wall sections 11a and 11b are preferably made of a transparent resinous material such as polystyrene. The interior surfaces of the wall sections 11a and 11b are coated with a hydrophilic coating 12. In practice, the hydrophilic coating 12 comprises a coating sold under the trade designation "HYDROMER" which is a polyurethane polyvinyl pyrollidone interpolymer manufactured by Biosearch, Whitehouse, New Jersey. Note that in some applications it may be desirable to add a hydrophilic additive directly to the resinous material of the wall sections so as to avoid the need to coat the surfaces with a hydrophilic coating.

The wall sections 11a and 11b provide two interior baffles 13 and 14. The baffles 13 and 14 along with the exterior walls of the container 11 make up an interior chamber which defines a cavity 15. The chamber has an upper portion with an inlet opening 16. The inlet opening 16 is suitable to be connected to a tube 17 that carries the liquid, the flow rate of which is to be measured, into the cavity 15. The tube 17 may be connected to a catheter (not shown) such as a Foley-type catheter, which is in-dwelling in a patient so that the liquid, such as urine, can flow from the patient through the catheter and the connecting tube 17 and into the container 11. The upper portion of the interior chamber is also provided with a vent opening 18, preferably above the inlet 16. In the container 11, the vent opening 18 admits air at atmospheric pressure into the interior cavity 15.

The baffle 13 and the right hand portions of the exterior walls of the container 11 make up a first conduit which defines a first passageway 19. The passageway 19 extends for substantially the entire height of the cavity 15 and opens into the cavity 15 well below the inlet and vent openings at a lower opening 20 which is relatively closely adjacent to the bottom of the container 11. The passageway 19 also has an upper opening 21 which opens to the exterior of the container 11. The upper opening 21 is thereby in communication with the cavity 15 below the inlet opening 16 and the vent opening 18.

The upper opening 21 is suitable to easily mount a pressure transducer 22 in operative relationship so that the upper opening 21 is sealed by the transducer 22 and the transducer 22 can measure the air pressure within the passageway 19. The transducer 22 provides an electrical signal in accordance with the air pressure in the passageway 19. The transducer should be capable of following the air pressure as closely as possible to provide a near instantaneous indication thereof. Note that this arrangement shields the pressure transducer 22 from urine contamination so that it need not be cleaned and is reuseable.

Either gauge or absolute pressure could be sensed by the pressure transducer 22. However, as will become clear from the following description, it is preferable to sense gauge pressure since atmospheric pressure acts on the liquid within the cavity 15. If absolute pressure were measured, the atmospheric pressure would be taken account of in the processing required to convert the pressure signal into a volume. A transducer 22 which was found suitable in practice is the transducer sold under the trade designation Microswitch No. 142PC01G. This transducer has a measuring port 22a and a gauge port 22b. In practice, the measuring port 22a is mounted to the opening 21 and the gauge port 22b is left open to the atmosphere to measure gauge pressure.

As liquid is admitted into the cavity 15 through the inlet opening 16, the level of liquid within the cavity rises. When the level of liquid in the cavity is below the lower opening 20, the pressure in the passageway 19 will be equal to atmospheric pressure due to the atmospheric vent 18. However, when the level of liquid rises above the opening 20, the passageway 19 becomes sealed from atmospheric pressure by the liquid. As the level of liquid in the cavity 15 rises above the opening 20, some of the liquid will enter the passageway 19 thereby compressing the air in the passageway and the air pressure in the passageway 19 will rise. The air pressure within the passageway 19 will depend upon the height of the liquid within the cavity 15 above the opening 20 which, in turn, is dependent upon the volume of the liquid within the container 11. Therefore, any given volume of liquid within the container 11 will produce a corresponding air pressure within the passageway 19.

While the air pressure within the passageway 19 can be used to determine the volume of liquid within the container 11, it can also be applied to determine the rate of change of the volume of liquid within the container, which equals the flow rate into the container. Designating the volume of liquid within the container as V, the flow rate into the container as F and time as t, the flow rate is related to the change in volume, or $\Delta V$, by the following relationship:

$$F = \frac{\Delta V}{\Delta t}$$

so that $$\Delta V = F \Delta t.$$

Now, designating the area occupied by the free surface (the surface exposed to atmospheric pressure) of the liquid within the container 11 by A, and assuming A to be constant for the height of the container above the opening 20 to simplify the analysis, and designating the height of the liquid level above the opening 20 by h, the change in volume $\Delta V$ is related to the change in height $\Delta h$ as follows:
ti $\Delta V = A \Delta h$, therefore $A\Delta h = F \Delta t$ so that $$\frac{\Delta h}{\Delta t} = \frac{F}{A}.$$

$\Delta V$ is not exactly equal to $A\Delta h$ because as the level of the liquid surface rises, some of the liquid will enter the passageway 19 to further compress the air therein. This introduces an approximation into the analysis but can be made negligible if the cross sectional area of the passageway 19 is small compared to the cross sectional area of the free surface of the liquid. Also, the error attributable to this approximation can be eliminated by the processing techniques explained below.

The rate of change of the height of the liquid level is represented by $\Delta h/\Delta t$. Therefore if A is substantially constant, it is shown that the rate of change of the height of the liquid level within the container 11 is directly proportional to the flow rate, F. Since the air pressure in the passageway 19 varies in accordance with the height of liquid within the cavity 15, the rate of change of the air pressure within the passageway 19 can be used as an indication of the flow rate into the cavity 15.

As previously mentioned, the output signal of the transducer 22 represents the instantaneous air pressure within the passageway 19. This signal could be input to a strip chart recorder or other output means to provide a graphical depiction of the pressure within the passageway 19 over a period of time. Since the graph would depict the pressure over time, one could get an indication of the rate of change of the pressure and therefore of the rate of change of the volume in the container 11 at a given instant by observing and/or measuring the slope of the graph at that instant.

Also, as previously mentioned, the output signal of the transducer 22, which is representative of the air pressure within the passageway 19, can be used to determine the height of liquid within the container 11 and can therefore also be used to determine the flow rate into the container. The exact relation between the air pressure in the passageway 19 and the height of the free surface of the liquid above the opening 20 is complicated by the fact that air is a compressible gas so that a change in the height of the free surface of the liquid causes some of the liquid to enter the passageway 19. While this complicates the relationship, the relationship is derivable and once derived, could be used to convert the air pressure in the passageway 19 into the height of the free surface or into the volume of the liquid within the container. The derived height or volume function could then be differentiated with respect to time to determine the flow rate.

However, it is not necessary to derive the relationship between the air pressure in the passageway 19 and the height or volume of the liquid within the container 11. It is not necessary because any volume of liquid of a given density within the container 11 which has a free surface above the opening 20 produces an air pressure within the passageway 19 which is repeatable. That is, for a known volume of liquid within the container 11, the air pressure within the passageway 19 can be experimentally measured. This can be repeated for many different known volumes of liquid and the resulting air pressures can be measured and recorded. Then later, when the volume within the container of the same liquid or of a liquid with substantially the same density is desired to be determined, the air pressure in the passageway 19 can be measured and compared with the earlier experimentally obtained results to obtain the volume of the liquid. This can be done for a series of unknown volumes and the resulting volume-time function can then be differentiated, such as by measuring the slope of the function at a given time, to yield the flow rate.

While this method of manually determining the flow rate is possible, it is tedious and time consuming. Therefore, a processor 23 is provided to convert the pressure transducer output signal into the flow rate. The pressure transducer 22 is connected to an analog to digital converter 24 which converts the pressure transducer output signal into a digital signal which is suitable to be input to a central processing unit 25. The central processing unit 25 is programmed to convert the digitized pressure signal into a flow rate and to output the flow rate.

Figure 3:
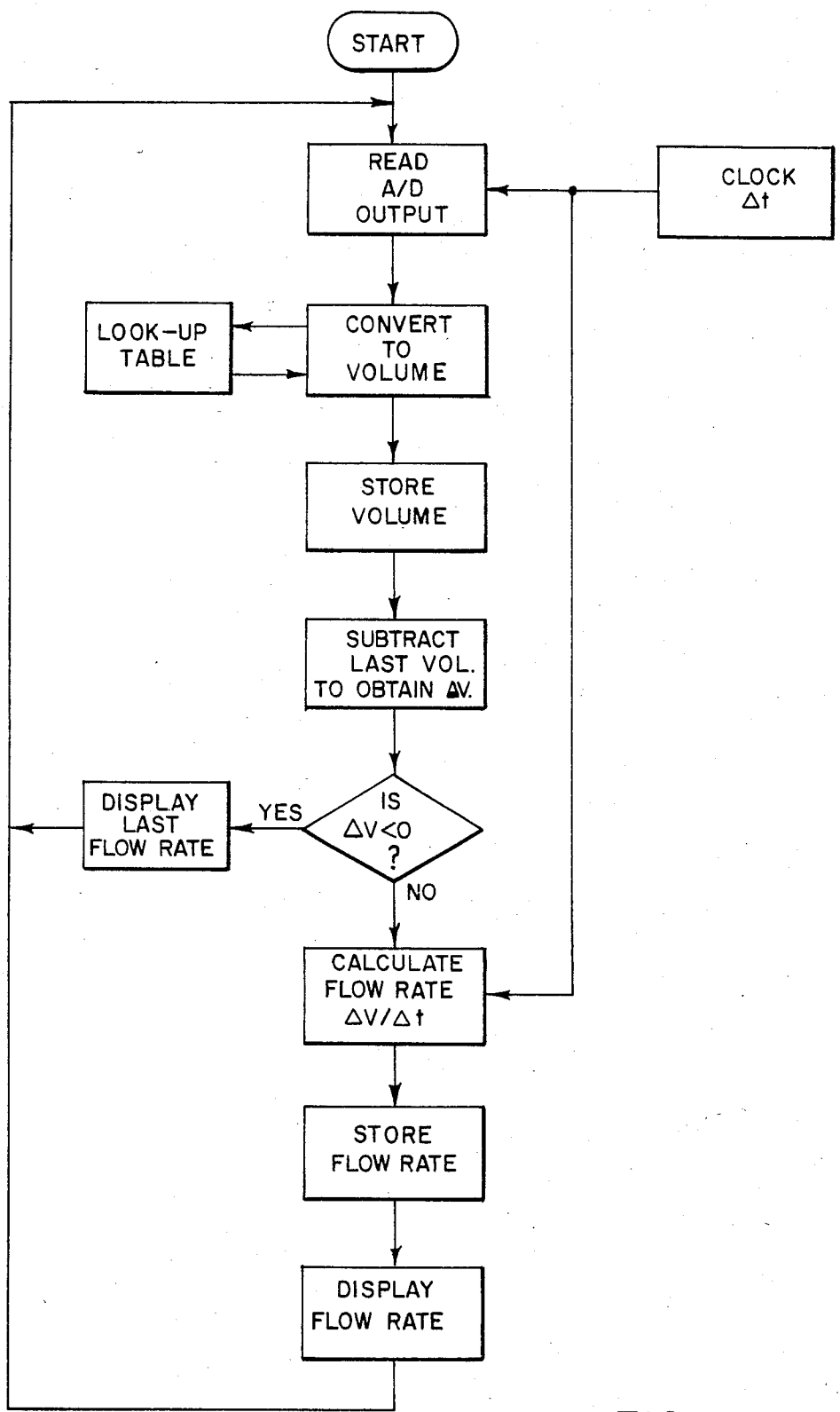
FIG. 3 is a flow chart of a program for the processor of the fluid flow meter of FIG. 1.

Referring to FIG. 3, the preferred processing technique employs a central processing unit 25 which has an internal clock which can generate a read signal at set intervals such as the microcomputer sold under the trade designation Intel 8051. The processing unit is programmed to await the signal from the internal clock to begin the portion of the program wherein the pressure signal is read and processed into the flow rate. The first step in this portion of the program is to generate an enable signal to be carried by an enable line 26 to the analog to digital converter 24. The analog to digital converter 24 would then convert the pressure signal from the transducer 22 into a digital signal which would be carried by a data bus 27 to the processing unit 25 where it is read.

The CPU 25 converts the digitized pressure signal into a volume using a look-up table. In the look-up table, the experimentally derived pressure-volume data is stored in associated memory addresses. The processor compares the input pressure value to the stored pressure values and stores the memory address of the experimental pressure value which is closest to the input pressure value. The processor then reads the volume from the memory address corresponding to the memory address of the closest experimental pressure value.

Returning to the mainstream of the flowchart in FIG. 3, the corresponding volume is stored in a third register. Each value stored in an address in the third register is separated in time from the immediately adjacent values by the time period between read signals from the internal clock. Therefore, the flow rate can be computed by taking the difference between two successive values and dividing it by the time period between the two values. For reasons to become apparent below, if the change in volume is negative, that is, if the volume in the container 11 decreases, it is desirable to disregard the change. In that case, the processor outputs the last flow rate and returns to await the next read signal.

If the change is zero or positive, the change in volume $\Delta V$ is divided by the time interval between read signals $\Delta t$ to yield the flow rate. The flow rate is then stored and displayed, and the processor returns to await the next read signal from the internal clock.

While any of a number of well known displays could be used, the preferred display is a strip chart recorder 30 to provide a histogram of the flow rate. The recorder 30 is interfaced to the CPU 25 by a digital to analog converter 31. When the CPU 25 reaches the display instruction in the program, it generates an enable signal which is carried by line 32 to the digital to analog converter 31 and enables the converter 31 to read the digital flow rate from the data bus 27. The converter 31 then converts the digital flow rate signal into an analog signal which is suitable for input to the recorder 30 via line 35. Also, the recorder 30 could be provided with an alarm which would light or sound whenever the flow rate was not within a preselected range.

The foregoing description adequately describes a container of the present invention. However, as liquid enters the container 11, the container 11 would eventually fill up and the liquid would exit the container via the vent opening 18 without other means provided. Therefore, in the preferred embodiment, the baffle 14 and the left hand portion of the exterior walls of the container 11 make up a second conduit which defines a second passageway 36. The second passageway 36 has a lower outlet opening 37 which opens into the cavity 15 above the lower opening 20 of the first passageway 19. The second passageway 36 also has an upper outlet opening 38 which is below the upper opening 21 of the first passageway 19 and opens to the exterior of the container. The upper outlet opening 38 is suitable to be connected to a drainage tube 40 which extends below the upper outlet opening 38 to a lower end (not shown). The lower end of the drainage tube 40 is below the lower outlet opening 37 and is connected to a drainage bag (not shown).

The second passageway 36 is provided so that the container 11 will automatically be partially drained. As liquid enters the container 11 and the level of liquid within the cavity 15 rises, the level of liquid within the passageway 36 will rise with it. Eventually, the liquid level within the passageway 36 will reach the level of the outlet opening 38. When this occurs, the liquid will exit the container 11 via the drainage tube 40 and create a suction which draws the level of the liquid within the cavity 15 down to the level of the lower outlet opening 37 by siphon action.

It should be noted that the area of the container 11 above the lower opening 37 and below the upper opening 38 is constant. This may be desirable in those applications where a derived equation is used to convert the pressure transducer 22 output signal into the flow rate to simplify the calculations. However, with the preferred processing technique of FIG. 3, this is irrelevant.

As the container 11 is drained by siphon action via the passageway 36, the liquid level within the cavity 15 will fall thereby causing the air pressure within the passageway 19 to fall. Any output attributable to the falling pressure would be meaningless and would be simply disregarded by an observer. However, in the preferred technique of FIG. 3, the processor disregards any negative changes in volume. It simply outputs the last flow rate and returns to await another read signal from the clock, as described above.

The container 11 can be inexpensively manufactured from injection molded polystyrene, thus, the cost of the container can be made low so that it is economical to dispose of the container after use. By making it economical to dispose of the container, the need for cleaning the container is obviated.

Figure 4:
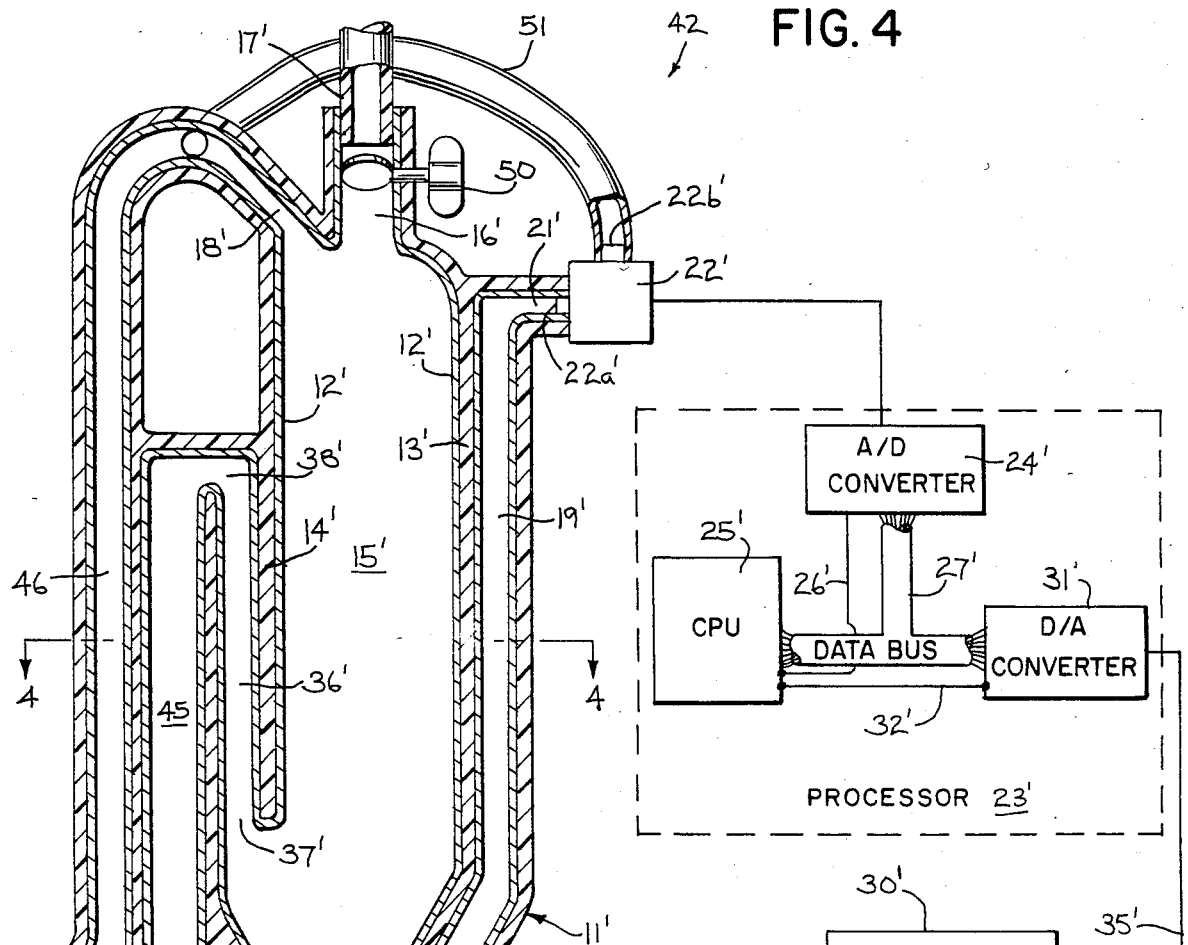
FIG. 4 is a block diagram of a meter pump apparatus for measuring the rate of fluid flow therethrough and for precisely metering the fluid flowing therethrough.
Figure 5:
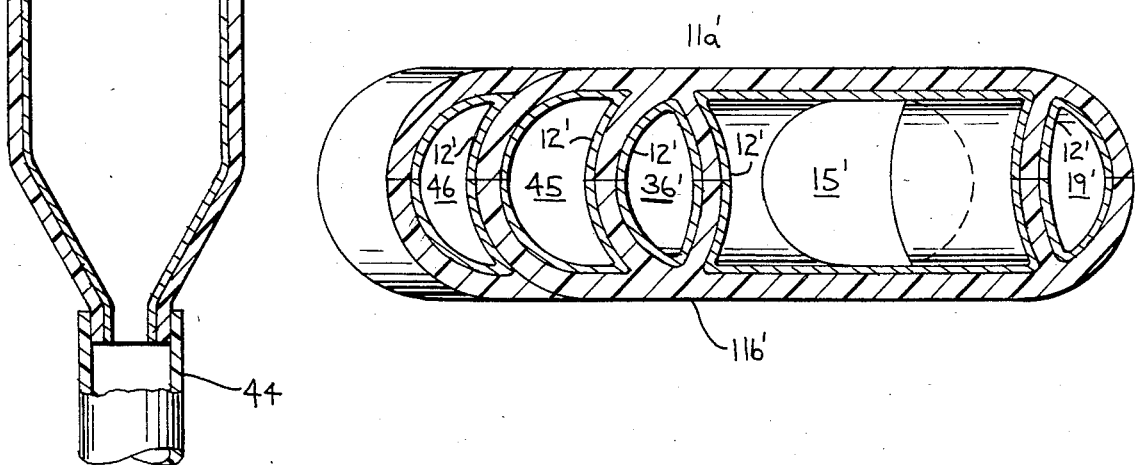
FIG. 5 is a cross-sectional view of the container of the meter pump apparatus of FIG. 4 taken along the plane of the line 4—4 thereof.

Although the flow measuring apparatus 10 is intended for flow measurement, the apparatus 10 can be modified as illustrated in FIGS. 4 and 5 to provide a meter pump 42 which not only measures the flow rate of an intravenous liquid but also precisely pumps the liquid into the patient without complex and expensive equipment. The entire description thus far pertains to the meter pump 42. Therefore, like elements have been designated with corresponding numerals. However, the meter pump 42 comprises structure in addition to the flow measuring apparatus 10 so that further description is necessary.

The container 11' of the meter pump 42 is also made in two pieces 11a and 11b with all inside surfaces covered with a hydrophilic coating 12'. The container 11' further comprises wall sections which define a second cavity 43 which is located below the lower opening 37'. The lower end of the wall sections defining the cavity 43 are suitable to be connected to a feed tube 44 which is to carry the liquid from the container 11' to the desired destination, such as a patient, below the cavity 43.

The upper end of the cavity 43 is in communication with the cavity 15' via a siphon passageway 45 and an equalizer passageway 46. The siphon passageway 45 is in communication with the passageway 36' and has an end opening 47 which is below the opening 37' of the passageway 36'. The conduits forming the equalizer passageway 46 are integral with those forming the vent opening 18' so that the passageway 46 is in communication with the vent opening 18'.

Note that it is not necessary that any of the conduits forming the various cavities and passageways of the containers 11 and 11' be integral with one another. However, it is necessary that the container 11 be open to the atmosphere, as provided by the vent opening 18, and that the container 11' be closed to the atmosphere, as will become apparent.

The meter pump 42 must be primed, preferably before the tube 44 is connected to a patient. Priming can be accomplished by the use of a flow control valve 50. The tube 17' is connected to a liquid source, such as an intravenous fluid bag, and the valve 50 is adjusted to allow a free flow of liquid into the cavity 15'. Any time after the level of the liquid in the cavity 15' surpasses the opening 38' and the liquid begins to exit the cavity 15' by siphon action via passageways 36' and 45, the valve is adjusted to provide a restriction to the flow through the inlet 16'. The liquid exiting the cavity 15' will collect in the cavity 43 and in the tube 44. Some of the liquid first exiting the cavity 15' will also be expelled out the patient end (not shown) of the tube 44.

However, not all of the liquid exiting the cavity 15' will be immediately expelled. As some of the liquid is expelled, a partial vacuum will develop in the cavity 43 which is communicated to the cavity 15' by the passageway 46. Eventually the vacuum will be sufficient to support the column of liquid in the tube 44 and the cavity 43. When this equilibrium vacuum is reached, the flow rate of the liquid expelled from the tube 44 will be exactly equal to the flow rate of the liquid entering the cavity 15' via the tube 17'. Since the flow rate of the liquid entering the cavity 15' can be adjusted by the control valve 50, the flow rate of the liquid being expelled from the tube 44 is adjustable. Once an uninterrupted flow of liquid (there may at first be air bubbles in the tube 44) is being expelled from the tube 44, the tube can be connected to the patient or other receptacle.

The meter pump 42 is referred to as a "pump" for the following reasons. Once the partial equilibrium vacuum is developed in the cavities 15' and 43, the flow rate of liquid into the cavity 15' will "pump" a like flow rate out of the cavity 43 to maintain the total volume of air and liquid in the container 11' constant. For example, immediately after the liquid has been siphoned from the cavity 15' into the cavity 43, the volume of liquid in the cavity 15' is at a steady state minimum value and the volume of liquid in the cavity 43 is at a steady state maximum value. If one drop of liquid is then admitted to the cavity 15' from the tube 17', it will displace a like volume of air in the cavity 15' which will momentarily cause the air pressure in the cavity 15' to rise. This pressure increase is communicated to the cavity 43 by the equalizer passageway 46 which causes a drop of liquid to be expelled from the cavity 43 out through the tube 44. Note that the drop admitted to the cavity 15' increases the volume, and therefore the height, of the liquid in the cavity 15, and that the drop expelled from the cavity 43 diminishes the volume in the cavity 43. However, when the height of liquid within the cavity 15' reaches the opening 38', the volume of liquid in the cavity 43 is replenished by siphon action, and the pumping cycle starts over again.

While this pumping is taking place, the meter portion of the meter pump 42 is operating as described in connection with the flow measuring apparatus 10. However, the meter pump 42 differs from the apparatus 10 in that it is not open to the atmosphere. Instead, the meter pump 42 is a closed system in which a partial vacuum acts on the liquid in the cavity 15'. Since the most relevant pressure value is the pressure attributable to the height of liquid within the cavity 15', which is equal to the difference between the air pressure in the passageway 19' and that in the cavity 15', it is desirable to directly measure that difference. This can be accomplished by providing communication between the gauge port 22b' of the pressure transducer 22' and the passageway 46 with a tube 51. Alternatively, as with the apparatus 10, the air pressure in the cavity 15' could be measured and input to the processor where it would be accounted for.

Note that the flow control valve 50 could be controlled by the processor 23' in a feed back type of control. This may be desirable in applications where a very accurate and constant flow rate is required. For this type of control, the control valve 50 would have an input which was connected to a digital to analog converter of the processor 23'. The desired flow rate would be programmed into the processor 23' and it would compare the measured flow rate to the desired flow rate to determine the correction signal to be input to the flow control valve 50 via the digital to analog converter.

It is important to understand that the container 11' is completely sealed from the atmosphere and therefore from contaminants. Thus, the sterility of the liquid flowing through the container 11' is assured, thereby reducing the possibility of infection.

Many modifications and variations of the invention will be apparent to those skilled in the art. It is therefore intended that the scope of the invention is not to be determined by the description of the preferred embodiments, but by the claims which follow.

I claim:

1. A disposable container for use in a meter pump apparatus in which a pressure transducer produces a signal which is proportional to an air pressure within the container which varies in accordance with the volume of liquid within the container, comprising:

an interior chamber defining a first cavity and having an upper portion with an inlet opening for admitting the liquid into the first cavity;

an integral first conduit defining a passageway and having a lower opening which opens into the first cavity below the inlet opening and an upper opening which is suitable to operatively mount the pressure transducer so that the upper opening is in communication with the first cavity below the inlet opening and the air pressure in the first passageway varies in accordance with the volume of liquid in the first cavity when the level of the liquid is above the lower opening of the first passageway and the upper opening of the first passageway is sealed by the pressure transducer;

an integral second conduit defining a second passageway and having a lower outlet opening in communication with the first cavity above the lower opening of the first passageway and an upper outlet opening below the upper opening of the first passageway;

an integral second chamber defining a second cavity below the upper outlet opening of the second conduit and having a lower opening which is suitable for connection to a feed tube;

an integral third conduit defining a third passageway between the upper outlet opening of the upper portion of the second passageway and the upper portion of the second cavity;

an integral fourth conduit defining a fourth passageway between the upper portion of the first cavity and the upper portion of the second cavity for providing communication between the first cavity and the second cavity so that when the second cavity is primed with a quantity of liquid, a partial vacuum is developed in the container and the admission of liquid into the first cavity pumps a similar quantity of liquid from the second cavity and liquid is transferred from the first cavity to the second cavity by siphon action when the level of liquid within the first cavity reaches the upper outlet opening of the second passageway; and means for controlling the flow of liquid into the first cavity to meter the volume of liquid pumped from the second cavity.

2. A disposable container as in claim 1, further comprising:

means for communicating the air pressure in the first cavity to the pressure transducer.

3. A disposable container for use in a meter pump apparatus in which a pressure transducer produces a signal which is proportional to an air pressure within the container which varies in accordance with the volume of liquid within the container, comprising:

an interior chamber defining a first cavity and having an upper portion with an inlet opening for admitting the liquid into the first cavity;

an integral first conduit defining a passageway and having a lower opening which opens into the first cavity below the inlet opening and an upper opening which is suitable to operatively mount the pressure transducer so that the upper opening is in communication with the first cavity below the inlet opening and the air pressure in the first passageway varies in accordance with the volume of liquid in the first cavity when the level of the liquid is above the lower opening of the first passageway and the upper opening of the first passageway is sealed by the pressure transducer;

an integral second conduit defining a second passageway and having a lower outlet opening in communication with the first cavity above the lower opening of the first passageway and an upper outlet opening below the upper opening of the first passageway;

an integral second chamber defining a second cavity below the upper outlet opening of the second conduit and having a lower opening which is suitable for connection to a feed tube;

an integral third conduit defining a third passageway between the upper outlet opening of the upper portion of the second passageway and the upper portion of the second cavity;

an integral fourth conduit defining a fourth passageway between the upper portion of the first cavity and the upper portion of the second cavity for providing communication between the first cavity and the second cavity so that when the second cavity is primed with a quantity of liquid, a partial vacuum is developed in the container and the admission of liquid into the first cavity causes the expulsion of a similar quantity of liquid from the second cavity and liquid is transferred from the first cavity to the second cavity by siphon action when the level of liquid within the first cavity reaches the upper outlet opening of the second passageway; and means for directly communicating the air pressure in the upper portion of the first cavity to the pressure transducer.

* * * * *